United States Patent [19]

Hilyard et al.

[11] Patent Number: 5,589,327
[45] Date of Patent: Dec. 31, 1996

[54] METHOD AND COMPOSITION FOR THE DETERMINATION OF RED BLOOD CELL FLOATE

[75] Inventors: Kathy Hilyard, Pembroke, Fla.; James Monticello, New City, N.Y.; James Rugg, North Miami, Fla.

[73] Assignee: Dade International Inc., Deerfield, Ill.

[21] Appl. No.: 276,293

[22] Filed: Jul. 18, 1994

[51] Int. Cl.$^6$ .......................... C12Q 1/00; G01N 33/53; G01N 33/48

[52] U.S. Cl. .................. 435/4; 435/29; 435/7.1; 435/177; 436/63; 436/74; 436/505; 436/520; 436/522; 436/172

[58] Field of Search ................. 435/4, 7.25, 7.9, 435/269, 7.1, 177; 436/505, 522, 521, 520, 519, 63, 74, 172

[56] References Cited

U.S. PATENT DOCUMENTS

| | | | |
|---|---|---|---|
| 3,988,431 | 10/1976 | Givas et al. | 436/18 |
| 4,136,159 | 1/1979 | Stone | 424/1 |
| 4,399,288 | 8/1983 | Riceberg | 436/18 |
| 5,242,832 | 9/1993 | Sakata | 436/17 |
| 5,250,437 | 10/1993 | Syouzdu et al. | 436/18 |
| 5,310,679 | 5/1994 | Artiss et al. | 436/18 |

FOREIGN PATENT DOCUMENTS 9208971   5/1992   WIPO.

OTHER PUBLICATIONS

Liu, Yong, "Assay of Erythrocyte Folate Content", pp. 688–692, (1974), (Micr Assay of Erythrocytic Folate Content by Aseptic Meth).
Proc. Natl. Acad. Sci. (1980), 77, (11) pp. 6368–6370. Hjelmeland, Leonard M. "A nondenaturing zwitterionic detergent for membrane biochemistry."
Pathology (1990), 22, pp. 82–87. Brown, Ross D. et al. Red Cell Folate Assays: Some Answers to Current Problems with Radioassay Variability.
Medical Laboratory Sciences (1987), 44, pp. 33–40. Gildis, C. R. and Dunbar, D. R. Measurement of low serum and red cell folate levels: a comparison of analytical methods.
Journal Clinical Pathology (1987), 40, pp. 393–397. Dawson, D. W. et al. Laboratory diagnosis of megaloblastic anaemia: current methods assessed by external quality assurance trials.
British Journal of Haematology (1974), 27, pp. 551–558. Schreiber, C. and Waxman, S. Measurement of Red Cell Folate Levels by 3H–Pteroylglutamic Acid (3H–PTeGlu) Radioassay.
Journal of Clinical Pathology (1966), 19, pp. 17–28. Hoffbrand, A. V. et al. Method of assay of red cell folated activity and the value of the assay as a test for folate deficiency.
Stratus® Folate Fluorometric Enzyme –Linked Assay Product Insert. Copyright 1993. Baxter Diagnostics Inc.
Quantaphase® B–12 Folate Radioassay; B–12 Radioassay; Folate Assay Instruction Manual. Apr. 1989. Copyright 1991. Bio–Rad Laboratories.
Simultrac–SNB Radioassay Kit Vitamin B12 [57–Co]/Folate [125–I] Summary and Explantation of the Test Handbook. Copyright 1992. Becton Dickinson and Co.
Ciba–Corning Immophase® Vitamin B12 [57 Co]/Folate [125I] Radioassay Product Insert. Rev H, May 1990.
Ciba–Corning ACS™ Folate Product Insert. Ciba–Corning. (1990).
SimulTrac–SNB Radioassay Kit Vitamin B12[57–Co]/Folate [125–I] Summary and Explanation of the Test Handbook. Effective Sep. 1989. Becton Dickinson and Co.
DualCount® Solid Phase No Boil Assay for Vitamin B12/Folic Assay Package Insert. D784 Jun. 21, 1990. Diagnostic Product Corporation.

*Primary Examiner*—John Kight
*Assistant Examiner*—Louise N. Leary
*Attorney, Agent, or Firm*—Cynthia G. Tymeson

[57] ABSTRACT

A composition is described which is useful in the assay of folate from a hemolysate prepared from red blood cells using non-radiolabeled assay techniques such as fluorometric, colorimetric, enzymatic or chemiluminescent assay methods. Methods to ready hemolysates for the assay of folate are also described.

22 Claims, 4 Drawing Sheets

METHOD AND COMPOSITION FOR THE DETERMINATION OF RED BLOOD CELL FLOATE

FIELD OF THE INVENTION

The present invention relates to methods and compositions useful in the determination of red cell folate. More particularly, the present invention relates to a method of sample preparation for the determination of the concentration of red cell folate using non-radiolabeled assay techniques and compositions useful for measuring the concentration of red cell folate using non-radiolabeled assays.

BACKGROUND OF THE INVENTION

Measurement of folate in humans Is important because folate deficiency is the predominant form of nutritional anemia. Other forms of nutritional anemia are vitamin B12 deficiency and iron deficiency.

Folate levels may be measured in serum or red cells. Red cell folate concentrations are thought to show a better correlation with the presence of megaloblastic changes in erythrocytes than are folate serum levels. See, *Measurement of Red Cell Folate Levels by $^3$H-Pteroylglutamic Acid ($^3$H-PteGlu) Radioassay*, Shreiber, Carol and Waxman, Samuel; British Journal of Haematology, (1974) 27, 551.

Currently, measurement of red cell folate levels is performed using radioassay techniques and in older microbiological techniques. In the radioassay techniques, whole blood is diluted with ascorbic acid in order to hemolyze the red blood cells. See, *Measurement of low serum and red cell folate levels: a comparison of analytical methods*, Gilois, C. R. et al. Medical Laboratory Sciences (1987) 44, 33–40. Incubation is generally recommended and is usually about 90 minutes. Some procedures state that incubation is not required. In one procedure the hemolysate thus formed is further diluted with a protein diluent to mimic the concentration of protein found in standards. In other commercially available procedures, the hemolysate is used directly in the radioassay.

The hemolysates may then be run in radioassays for folate. Generally, the sample is combined with a known quantity of $^{125}$I labeled folate with dithiothreitol and incubated. In some procedures which also assay for Vitamin B12 the solution is boiled. The mixture is then combined with folate binding protein. During an incubation step, the labeled folate competes with the folate in the sample for the folate binding protein. The solution is centrifuged and decanted. The red cell membrane is decanted off. The radioactivity of a pellet containing the folate is counted using standard techniques and the results compared to standards.

Radioassays suffer from the disadvantage that these assays use radioactive labels and the waste from these labels must be disposed of appropriately. These assays also have a number of long incubation steps.

Some commercially available radioassays include DPC DUALCOUNT SOLID PHASE NO BOIL ASSAY; Ciba Corning IMMOPHASE®; BECTON DICKINSON Simul-TRAC-SNB Radioassay Kit; and BIO-RAD Quantaphase® Radioassay.

Development of non-radiolabeled assays for red cell folate, and particularly non-radiolabeled assays for red cell folate that utilize an absorbent solid phase, presents a number of challenges. First, the red cells must be lysed so that the folate is released. Second, the folate must be stabilized. Third, the red cell membranes must be separated from the folate so that the membranes do not interfere with the measurement of folate Separation by decanting, such as in the radioassay techniques would generally not be practical or sufficient for non-radiolabeled assay techniques.

The term non-radiolabeled assay as used herein means that the assay uses a label, but the label is not a radioactive label. Thus, the types of radioassays and microbiological assays are not included in this definition of non-radiolabeled assays. The types of assays that are non-radiolabeled include assays that use as a label, for example, a chromophore, a fluorophore, an enzyme, or a chemiluminescent molecule.

In particular, separation by decanting is impractical and insufficient for heterogeneous non-radiolabeled assays that utilize adsorbent solid supports such as paper, cellulose, polymers, or glass fibers. Generally in these methods, sample is added to a solid support which contains, or will contain, a binding protein (e.g. an antibody or folate binding protein) that is reactive to a molecule that selectively binds to the binding protein (e.g. an antigen or folate). There are many variations in these procedures that are known to those skilled in the art. Usually as a final seep, the solid support is washed to remove unbound materials. However, red cell membranes are readily adsorbed by absorbent solid supports and are difficult to remove. In addition, depending on the pore size of the solid support, the membranes may occlude the pores. This occlusion prevents the flow of any wash solution and hence prevents the separation of unbound materials from bound materials. In addition, unwashed membrane may serve to bind enzyme conjugate leading to a higher background and depending on the signal molecule used in the assay, the membrane may contribute to the measured signal.

Currently there are commercially available non-radiolabeled based assays for the determination of serum folate. Examples of the available procedures include Baxter Diagnostics Inc. STATUS® Folate Assay, a fluorometric enzyme assay and Ciba Corning ACS™ Folate Assay, a chemiluminescent assay. Currently, red cell folate can not be measured by these techniques. For example, the ACS™ Folate Assay procedure notes as a limitation that hemolysis significantly increases folate values due to the high folate concentration in red blood cells. The Stratus® Folate Assay procedures also states that hemolyzed samples must not be used. Thus, hemolyzed samples are to be avoided in non-radiolabeled assays.

Methods and compositions are needed to overcome the difficulties associated with radioassays for red cell folate and to make the determination of red cell folate practical and accurate using non-radiolabeled techniques. See, *Red Cell Folate Assays: Some Answers to Current Problems with Radioassay Variability*, Brown, Ross D. et al. Pathology 22 pp. 82–87 (1990).

SUMMARY OF THE INVENTION

This invention provides a method of sample preparation for non-radiolabeled assay methods to measure red cell folate. In these methods the red cell membrane is solubilized to provide for sufficient removal of the membrane from the solid phase. In addition, compositions are provided to solubilize red cell membranes.

In the method of the invention, an aliquot of whole blood is diluted with a hemolysis solutions such as ascorbic acid to form a hemolysate. The preparation of hemolysates is known in the art. Next, sufficient amounts of the hemolysate are combined with a diluent containing a detergent to solubilize the membranes. The hemolysate can now be analyzed by standard non-radiolabeled assay techniques to measure folate.

The composition of this invention is an aqueous solution comprising a buffer, a detergent that can solubilize red cell membranes contained in the hemolysate without the formation of a precipitate, and a salt. The composition may contain a folate-free inert protein and a preservative. Alternatively, the appropriate detergent can be added to buffered reagents that are already utilized in current serum folate assays.

DETAILED DESCRIPTION OF THE INVENTION

Figure 1:
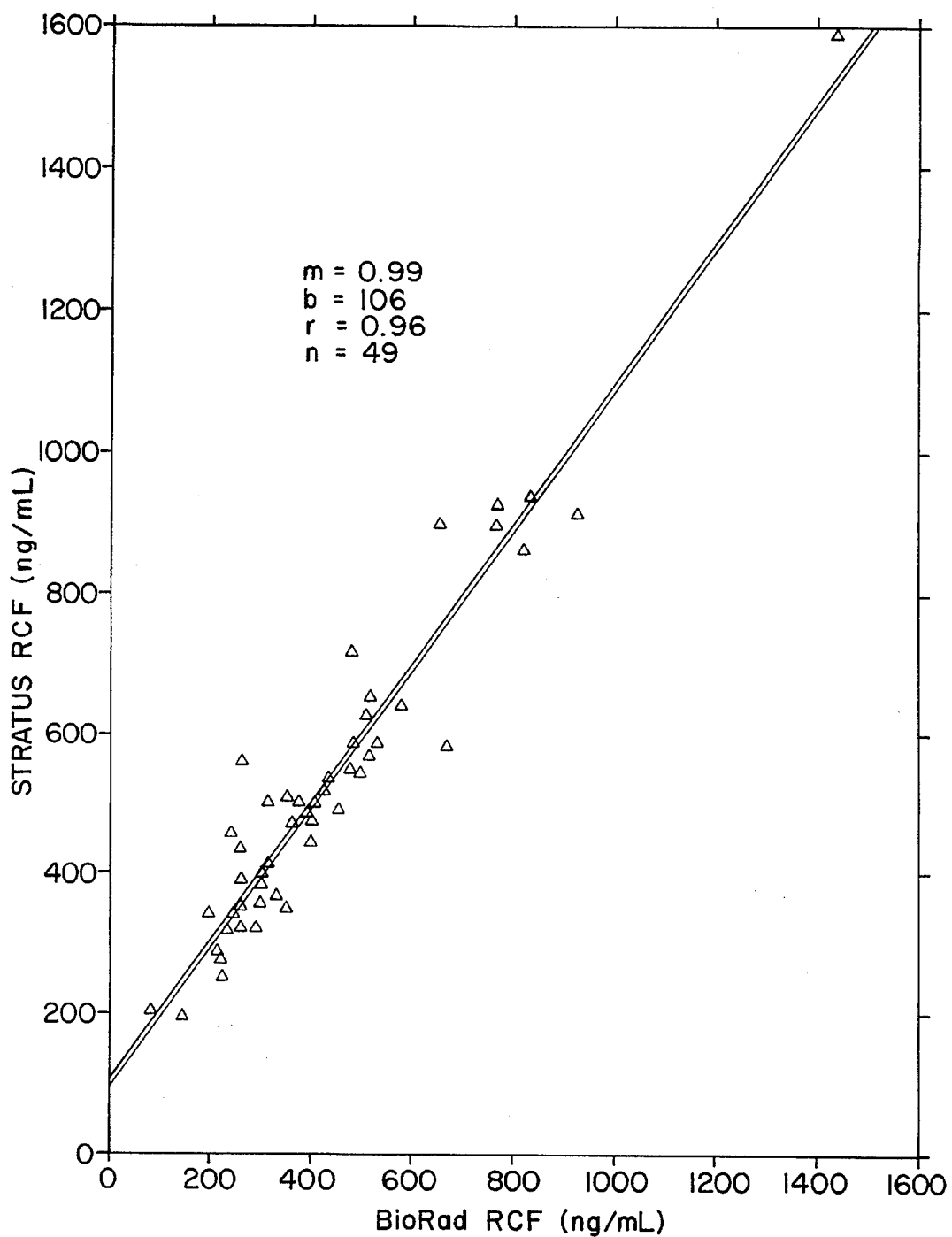
FIG. 1 shows patient sample results from an enzyme assay method for red cell folate of the present invention compared with a radioassay method.

The composition of the present invention comprises an aqueous solution of a detergent that can solubilize red cell membranes without the formation of a precipitate, a buffer, and a salt. The composition may contain a folate-free inert protein and a preservative.

The detergents of the present invention comprise those detergents that can solubilize red cell membranes and function in the final composition of the present invention to remove the membranes from the solid support. Preferably the solubilization occurs without the formation of a precipitate when the final composition containing the detergent is added to the hemolysate.

Detergents that are preferred include the zwitterionic detergents: (3-{3-cholamidopropyl)dimethyl-ammonio}-1-propanesulfonate) (hereinafter referred to as CHAPS), (3-[3-cholamidopropyl)-dimethylammonio-2-hydroxy-1-propanesulfonate) (hereinafter referred to as CHAPSO), and N-dodecyl-N,N-dimethyl-3-ammonio-1-propanesulfonate. Another detergent that was found to be acceptable was the non-ionic detergent n-Octyl-β-D-glucopyranoside (OTG), however OTG was not preferred because slight precipitation occurred when the final composition was added to the hemolysate.

The term acceptable, as used herein, means first that here is no more than a slight precipitation when the composition of the present invention is added to a hemolysate and second that the red cell folate values as determined in non-radiolabeled assays of the present invention are reasonably equivalent to those values that are obtained using commercially available radioassay methods. Reasonably equivalent means the correlation between methods is more than about 0.85, preferably more than about 0.90, and most preferably more than 0.95.

Detergents that were expected to work, but in fact did not work, were such non-ionic detergents as Tween-20, Brij-35, Nonidet P-40, Triton X-100, and POE coco amine. Although these detergents apparently solubilized the membranes (no precipitates were detected) these detergents were not acceptable. This was determined by substituting the above-mentioned detergents for detergents such as CHAPSO in the compositions of the present invention and performing a folate assay of the present invention on thirteen patient blood samples. The results were compared to a radioassay method using the same thirteen patient blood samples. It was found that about 70% of the samples that were tested recovered red cell folate levels that were greater than two times the results recovered from the radioassay method.

Other non-ionic detergents that were tried included glucopon 425 CS which is ($C_{6-12}$ alkylmono and oligoglucopyranosides, and $C_{10-16}$ alkylmono and oligoglucopyranosides) and POE(5) soya amine. The glucopon 425 CS formed a heavy precipitate when added to the hemolysate and the POE (5) soya amine formed an oily mixture when combined with the other materials of the compositions of the present invention. Thus, these detergents were unacceptable and were not evaluated in the enzyme assays for folate.

Other zwitterionic detergents that were tested but were found to be unacceptable were: N-octyl-N,N-dimethyl-3-ammonio-1-propanesulfonate and N-octadecyl N,N-dimethyl-3-ammonio-1-propanesulfonate. The N-octyl-N,N-dimethyl-3-ammonio-1-propanesulfonate when used in the composition of the present invention formed a precipitate when combined with the hemolysate. Thus, the composition containing this detergent was not evaluated in the enzyme assays for folate. The N-octadecyl N,N-dimethyl-3-ammonio-1-propanesulfonate was insoluble in aqueous solution. Thus compositions of the present invention could not be prepared with this detergent.

It is important to note that all of the compositions containing zwitterionic detergents that did not form precipitates when combined with hemolysates were found to be acceptable and indeed are preferred detergents of the present invention.

Other detergents may be tested for acceptability by using the preferred embodiment of the compositions of the present invention (as described below), but substituting the preferred detergents for the detergent to be tested. First, the composition containing the detergent must not form more than a slight precipitate upon combining the composition with the hemolysate, preferably the final sample is clear to the eye. Second, results of patient samples as obtained in non-radiolabeled assays should be reasonable equivalent to those results from commercially available radioassay methods.

The concentration of the detergent should be at least about 0.5%. The preferred concentration range is between about 1 and 3%. The most preferred concentration is about 2%. Combinations of detergents are acceptable.

The buffers of the present invention include, but are not limited to, TRIS, borate buffers, sodium or potassium phosphate buffers, 3-[N,N-bis(2-Hydroxyethyl)amino]-2-hydroxy-propanesulfonic acid (DIPSO), 3-[N-tris(hydroxymethyl)methylamino]-2-hydroxy-propanesulfonic acid] (TAPSO), N-[2-hydroxyethyl}piperazine-N'-[2-hydroxypropanesulfonic acid] (HEPPSO), Piperazine-N,N'-bis[2-hydroxypropanesulfonic acid] (POPSO), N-[2-hydroxyrthyl][piperazine-N'-[3-propanesulfonic acid} (EPPS), Triethanolamine (TEA), Tricine, Bicine, and N-tris[hydroxymethyl]methyl-3-aminopropanesulfonic acid; ([2-hydroxy-1,1-bis(hydroxymethyl)-ethyl]amino)-1-propanesulfonic acid) (TAPS).

The choice of buffer is not critical, however the preferred buffers are those buffers that have a pH buffering capacity at between about pH 8 to 10. The buffering capacity at this pH range is important because the assays for serum folate are conducted at about pH 9 to 9.5. The most preferred buffer is TRIS becasue of its availability. The preferred pH range is about 8 to 10 and most preferred is 8.5 to 9.5.

Buffers were tested at a variety of concentrations. The concentration of buffer was found not to be critical although it was found that some level of buffer was required. A composition which did not include a buffer gave folate results that were highly variable when one sample was repeatedly tested in an enzyme assay. The concentration of the buffer may be from about 0.01M to 1M. The preferred concentration of the buffer is about 50 mM to 200 mM.

A salt may also be added to the compositions. The salts that may be added to the compositions of the present invention include, but are not limited to, sodium chloride, potassium chloride, sodium sulfate, sodium bromide, potassium bromide, calcium chloride, barium sulfate, barium chloride, and lithium chloride. The most preferred salt is sodium chloride because of its availability and because of its compatibility with blood.

The concentration of the salt may be from about 0 to to over 0.5M. The preferred concentration is physiological concentrations of about 0.85%.

An inert protein may also be added to the composition. If protein is added to the composition, it is important that it is folate-free. The protein can be recombinant or native. The proteins that may be added include, but are not limited to, albumin, gelatin, ovalbumin. Bovine serum albumin is preferred because of its availability.

The protein may be added in concentrations from about 0 to over 10%. The preferred amount of protein is from about 0.5 to 5%. It is thought that protein may be required in order to obtain correct results for samples that have a low hematocrit, however a study of a limited number of samples that have a low hematocrit demonstrated that the protein did not affect the folate values.

For commercial embodiments, a preservative should be added to prevent the growth of bacteria and/or fungi. Common preservatives include sodium azide, gentamicin, nystatin, thimereasol, and kathon.

The compositions of the present invention may be prepared by combining effective amounts of detergent in buffer. The composition may include effective amounts of salt, protein and preservative. For example, a preferred composition was prepared as follows: To prepare one liter combine about 50 grams of folate-free bovine serum albumin to about 800 milliliters of a 50 mM solution of TRIS and 0.85% sodium chloride (TRIS Buffered Saline). The albumin was allowed to dissolve using gentle mixing while avoiding foaming. About 4 milliliters of a 25% solution of sodium azide was added while the solution was mixing. About 20 grams of CHAPS was added while the solution was mixing. Mixing was continued until the CHAPS was completely dissolved. The pH of the solution was adjusted to about 9.3 and the volume was adjusted to 1 liter with TRIS Buffered Saline. The solution was sterile filtered. It is important to note that the order of addition of the reagents is not important. Generally, the protein is added first because it takes the longest to dissolve.

In the method of the present invention, a composition is prepared as described above. Hemolysate samples are combined with the composition. The diluted hemolysate is assayed using commercially available non-radiolabeled assays kits for serum folate.

Alternatively, currently available assay kits contain reagents such as neutralizing or conditioning reagents. These neutralizing or conditioning reagents are appropriately buffered. For example, the ACS™ Folate Assay contains conditioning reagents such as the Folate Conditioning Reagent B which contains a BSA buffered solution and the Stratus® Folate Assay contains a Folate Neutralizer Reagent which is a tetraborate buffered solution. Thus, the detergents of the present invention can be added to these reagents and the sample can be assayed using the kit.

Hemolysate samples are prepared by making a 1:10 dilution to 1:50 dilution of whole blood with a solution of about 0.125% to 2% ascorbic acid solution. The preparation of hemolysate samples is known in the art. See, *Measurement of low serum and red cell folate levels: a comparison of analytical methods,* Gilois, C. R. et al. Medical Laboratory Sciences (1987) 44, 33–40. For instance, in the Bio-Rad Red Cell Folate Reagent Pack in combination with the Bio-Rad Quantaphase® B12/Folate Radioassay use a 1:11 dilution of blood to a 0.4% ascorbic acid solution and the DPC DUALCOUNT B12/Folate No Boil Assay requires that whole blood be diluted 1:21 with a 1% solution of ascorbic acid.

The hemolysate may be used fresh or stored frozen. If the hemolysates are to be used fresh an incubation period from about 0 to over 90 minutes at room temperature may be performed to ensure that the whole blood is completely hemolysed. The preferred incubation time is 30–90 minutes, and the most preferred incubation time is about 90 minutes.

In the method of the present invention, approximately equal amounts of the hemolysate are combined with the compositions of the present invention. Then the mixture is assayed in available non-radiolabeled assay techniques such as assay methods that utilize enzymes, colorimetric molecules, chemiluminescent molecules and fluorometric molecules as labels.

It is believed that the method to prepare samples for non-radiolabeled assays is most beneficial, but is not limited to, those assays that utilize absorbent solid phases listed above. Examples of the types of assays that use such solid phases include Baxter Diagnostics Inc. STRATUS® FLUOROMETRIC ASSAY SYSTEM; PB Diagnostic Inc. OPUS® Assay System and Abbott's ImX® Assay System.

The invention can be further understood by reference to the foregoing examples which are for illusuration only and are not to be construed as a limitation on the invention.

EXAMPLE 1

Preparation of Hemolysate Diluent
I. Materials:
  TRIS: molecular weight 121.1
  NaCl: molecular weight 58.44
  CHAPS: Sigma Chemical Co.
  Folate-free BSA: Intergen Inc.
II. Preparation of Stock Solutions
A. A stock solution of 20% folate-free BSA (FFBSA) and 8% CHAPS was prepared as follows: Twenty grams of FFBSA were added to 90 milliliters of distilled water and stirred gently until the FFBSA was completely dissolved. Eight grams of CHAPS were added to the FFBSA solution and stirred gently until the CHAPS was dissolved.

The total volume was brought up to 100 milliliters with distilled water. (Stock A)

B. A stock solution of 2M TRIS was prepared by adding 48.44 grams of TRIS to about 90 milliliters of distilled water and was stirred until the TRIS was dissolved. The total volume was brought up to 200 milliliters with distilled water. (Stock B)

C. A stock solution of 4M NaCl was prepared by adding 23.38 grams of NaCl to about 90 milliliters of distilled water and stirred until the salt was dissolved. The total volume was brought up to 200 milliliters with distilled water. (Stock C)

III. Preparation of the Hemolysate Diluent

One milliliter of Stock B and 1.5 milliliters of Stock C were added to 10 milliliters of Stock A. The pH of the solution was adjusted to 9.30±0.05. The volume of the solution was brought up to about 40 milliliters and the pH was rechecked. Final concentration of the diluent is about 50 mM TRIS, 150 mM NaCl, 2% Chaps, and 5% FFBSA.

EXAMPLE 2

Assay of Folate in Red Blood Cells and Comparison with Radioassay Methods

Fifty patient samples were prepared for assay of folate using a non-radiolabeled assay, the Stratus® Folate Assay and compared with two different radio-labeled assays, the DPC DUALCOUNT B12/Folate No Boil Assay and the BIO-RAD Quantaphase® B12/Folate Radioassay.

I. Preparation of Hemolysate Diluent

A. Materials:

TRIS: molecular weight 121.1
NaCl: molecular weight 58.44
CHAPS: Sigma Chemical Co.
Folate-free BSA (FFBSA): Intergen Inc.

B. A solution of 100 mM TRIS was prepared by dissolving 12.11 grams of TRIS in 1 liter of distilled water. About 8.76 grams of NaCl was added to an aliquot of 500 mls of the TRIS buffer to form 100 mM TRIS with 300 mM NaCl (TRIS Buffered Saline). Sodium azide was added to a final concentration of 0.2%.

About 0.25 grams of FFBSA were added to 50 milliliters of the TRIS Buffered Saline. The solution was stirred gently until dissolved to form TRIS Buffered Saline-BSA. Next about 0.5 grams of CHAPS were added to 25 milliliters of the TRIS Buffered Saline-BSA. The pH was adjusted to about 9.3. The final concentration is 100 mM TRIS, 300 mM NaCl, 0.5% BSA, 2% CHAPS and 0.2% Sodium Azide.

II. Preparation of Hemolysates from Blood

A. For the DPC folate assay an aqueous solution of 1.0% Ascorbic Acid (Aldrich) was prepared. One hundred microliters of blood was added to 2 milliliters of the ascorbic acid solution. The samples were stored frozen at −20C. until used in the assay in performed.

B. For the BIO-RAD folate assay an aqueous solution of 0.4% Ascorbic Acid (BIO-RAD) was prepared. One hundred microliters of blood from each sample was combined with 1 milliliter of the 0.4% ascorbic acid solution. The samples are stored frozen at −20 C. until the assay was performed.

C. For the Stratus folate assay an aqueous solution of 0.4% Ascorbic Acid (Aldrich) was prepared. One hundred microliters of blood from each sample was combined with 1 milliliter of the 0.4% ascorbic acid solution. The samples are stored frozen at −20 C. until the assay was performed.

III. Preparation of Samples for Assay from Hemolysates

A. For the DPC assay, the hemolysates were thawed and no further processing was required.

B. For the Bio-Rad assay, the hemolysates were thawed and 100 microliters of hemolysate was added to 100 microliters of Bio-Rad protein diluent.

C. For the Stratus assay, the samples were thawed and 100 microliters of the hemolysates were diluted with one hundred microliters of the Hemolysate Diluent, prepared as described in Example 2 Section I.

IV. Assay of the Samples

A. The samples as prepared in Example 2 Section IIIA, were assayed according to the package insert for the DPC assay. Appropriate controls were analyzed for the assay.

B. The samples as prepared in Example 2 Section IIIB, were assayed according to the package insert for the Bio-rad assay. Appropriate controls were analyzed for the assay.

C. The samples as prepared in Example 2 Section IIIC, were assayed according to the package insert for the Stratus assay. Each sample was assayed using two different Stratus kit lots. Appropriate controls were analyzed for the assay.

V. Results

TABLE 1

| Sample # | HCT | Bio-Rad | DPC | Stratus | Stratus |
|---|---|---|---|---|---|
| 1 | 23 | 478 | 584 | 723 | 669 |
| 2 | 31 | 390 | 427 | 490 | 454 |
| 3 | 39 | 350 | 538 | 355 | 327 |
| 4 | 23 | 373 | 347 | 507 | 459 |
| 5 | 28 | 196 | 195 | 346 | 314 |
| 6 | 44 | 260 | 535 | 395 | 314 |
| 7 | 35 | 352 | 444 | 515 | 484 |
| 8 | 43 | 261 | 352 | 353 | 327 |
| 9 | 22 | 240 | 277 | 460 | 410 |
| 10 | 34 | 1191 | 1365 | | |
| 11 | 26 | 330 | 355 | 372 | 338 |
| 12 | 27 | 652 | 747 | 904 | 847 |
| 13 | 51 | 315 | 325 | 418 | 393 |
| 14 | 25 | 475 | 470 | 554 | 510 |
| 15 | 47 | 407 | 456 | 505 | 477 |
| 16 | 35 | 817 | 762 | 867 | 817 |
| 17 | 21 | 262 | 290 | 566 | 513 |
| 18 | 33 | 507 | 490 | 633 | 593 |
| 19 | 48 | 426 | 429 | 522 | 495 |
| 20 | 32 | 481 | 1628 | 591 | 550 |
| 21 | 30 | 924 | 910 | 917 | 865 |
| 22 | 45 | 220 | 229 | 283 | 259 |
| 23 | 37 | 244 | 278 | 345 | 309 |
| 24 | 46 | 512 | 575 | 574 | 540 |
| 25 | 38 | 399 | 608 | 481 | 446 |
| 26 | 42 | 262 | 340 | 325 | 298 |
| 27 | 49 | 224 | 244 | 256 | 233 |
| 28 | 18 | 831 | 805 | 941 | 868 |
| 29 | 39 | 214 | 226 | 293 | 265 |
| 30 | 22 | 260 | 248 | 440 | 390 |
| 31 | 30 | 301 | 315 | 403 | 367 |
| 32 | 24 | 431 | 534 | 541 | 495 |
| 33 | 32 | 234 | 236 | 323 | 289 |
| 34 | 19 | 313 | 309 | 509 | 451 |
| 35 | 38 | 515 | 492 | 660 | 625 |
| 36 | 29 | 303 | 442 | 387 | 349 |
| 37 | 31 | 362 | 426 | 475 | 433 |
| 38 | 50 | 453 | 458 | 497 | 466 |
| 39 | 52 | 144 | 161 | 199 | 182 |
| 40 | 51 | 397 | 370 | 449 | 418 |
| 41 | 50 | 290 | 302 | 326 | 304 |
| 42 | 33 | 667 | 706 | 587 | 547 |
| 43 | 50 | 576 | 596 | 647 | 612 |
| 44 | 34 | 298 | 371 | 362 | 330 |
| 45 | 36 | 495 | 630 | 550 | 513 |
| 46 | 41 | 762 | 953 | 901 | 858 |

TABLE 1-continued

| Sample # | HCT | Bio-Rad | DPC | Stratus | Stratus |
|---|---|---|---|---|---|
| 47 | 21 | 765 | 950 | 932 | 869 |
| 48 | 36 | 79 | 93 | 208 | 177 |
| 49 | 20 | 1430 | 1187 | 1595 | 1518 |
| 50 | 37 | 529 | 868 | 589 | 553 |

Figure 2:
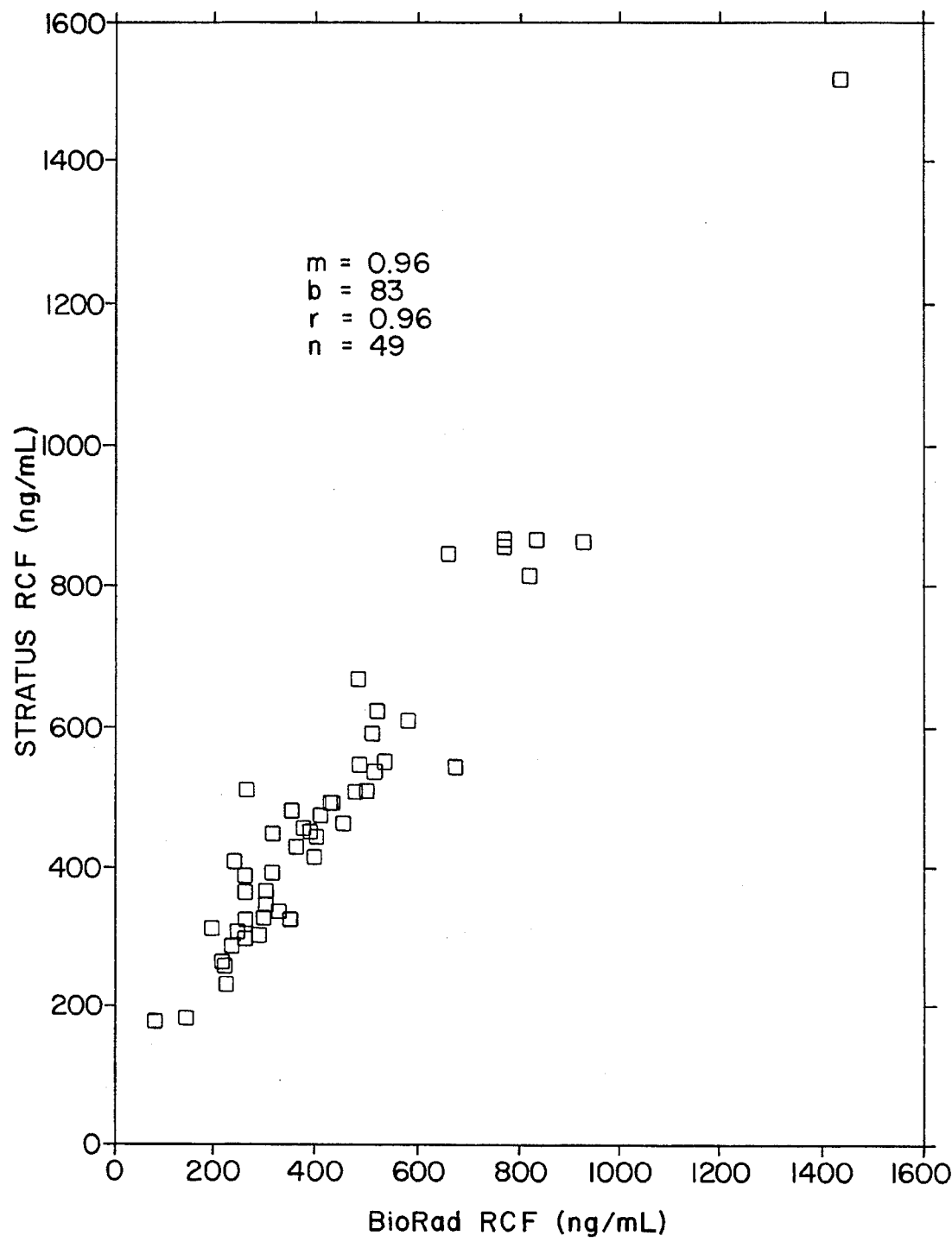
FIG. 2 shows patient sample results from an enzyme assay method for red cell folate of the present invention compared with a radioassay method.
Figure 3:
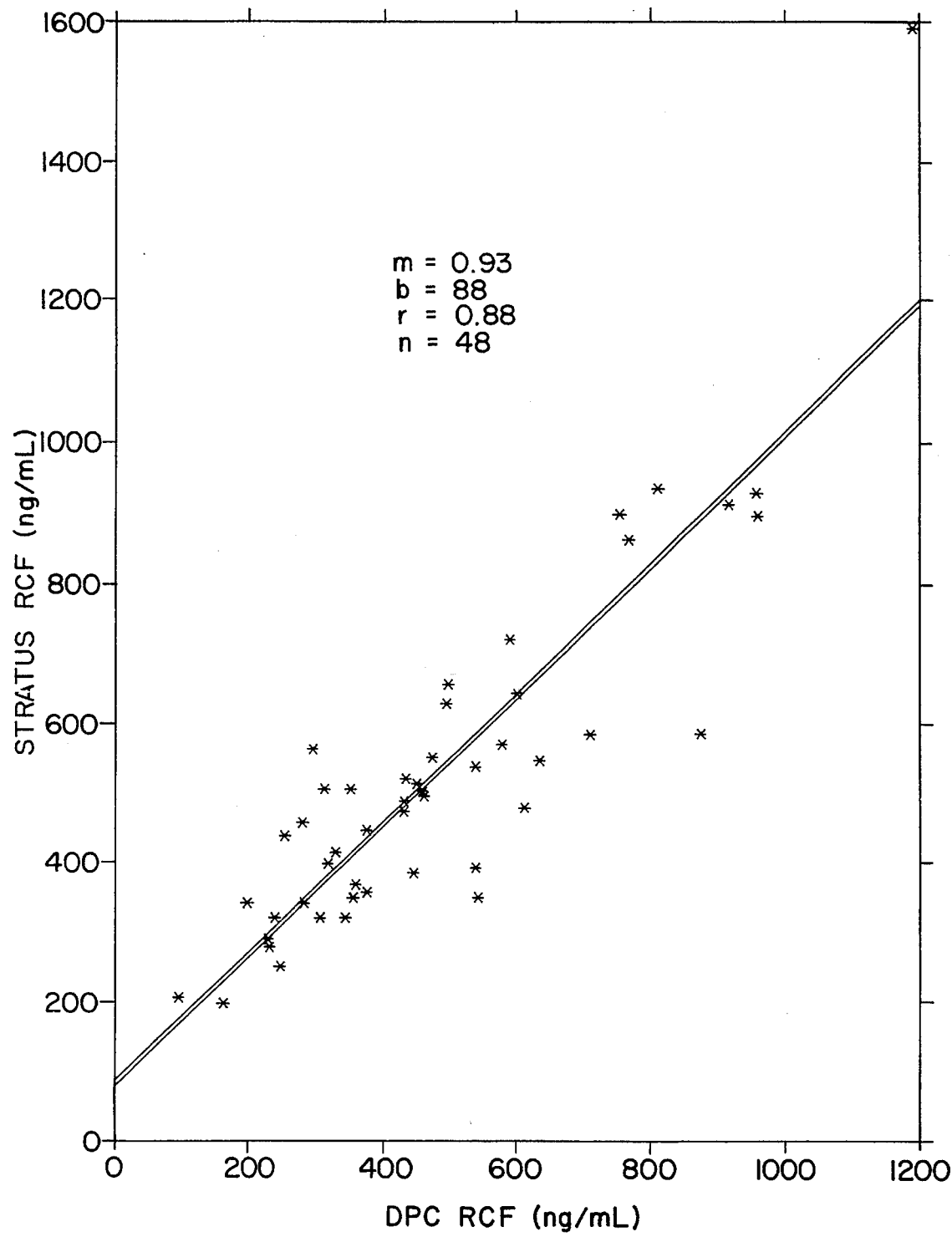
FIG. 3 shows patient sample results from an enzyme assay method for red cell folate of the present invention compared with a radioassay method.
Figure 4:
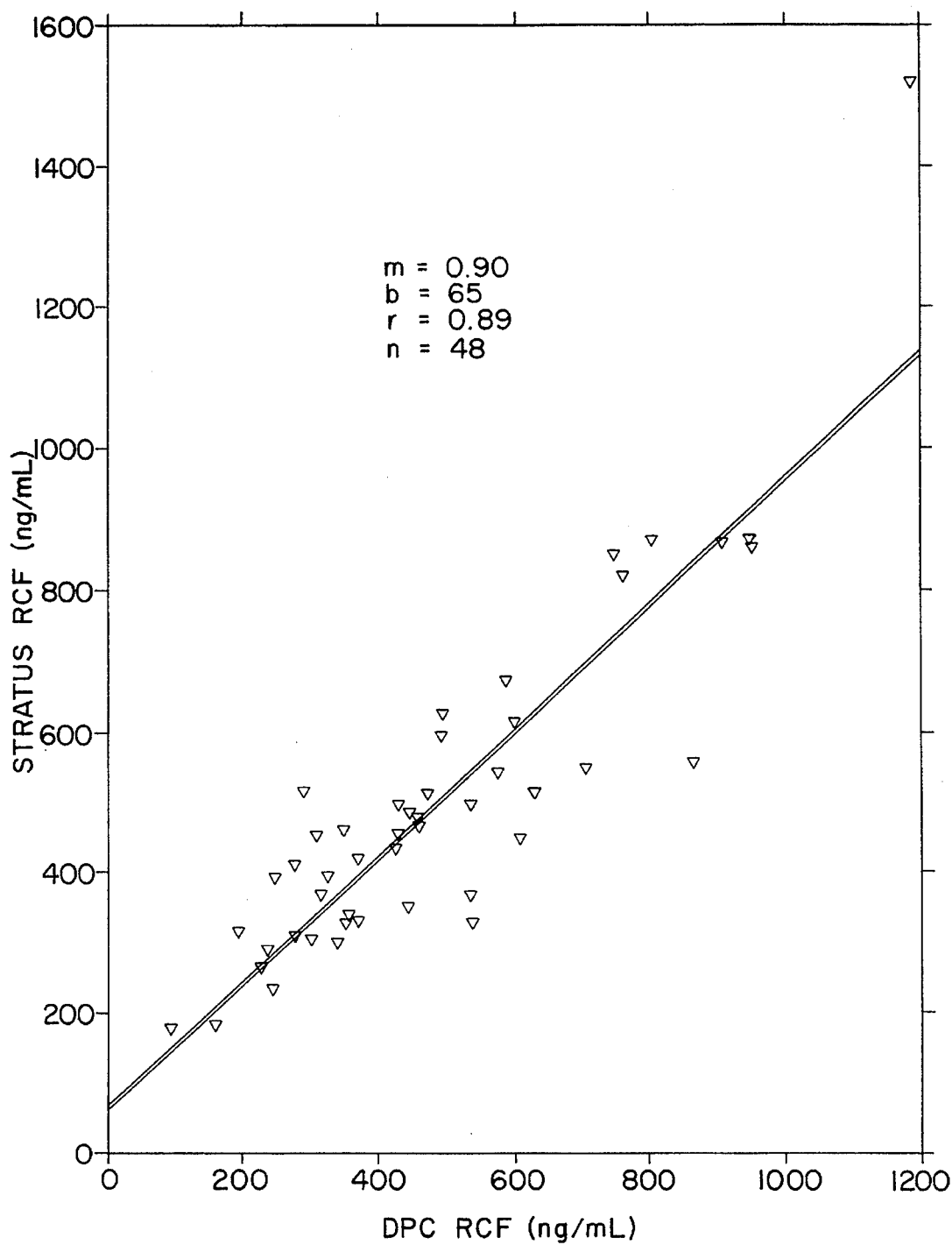
FIG. 4 shows patient sample results from an enzyme assay method for red cell folate of the present invention compared with a radioassay method.

Results are presented graphically in FIGS. 1–4.

EXAMPLE 3

I. Preparation of Hemolysate Diluent
A. Materials:
  TRIS: molecular weight 121.1
  NaCl: molecular weight 58.44
  CHAPS: Sigma Chemical Co.
  Folate-free BSA: Intergen Inc.
B. A solution of 100 mM TRIS is prepared by dissolving 12.11 grams of TRIS in 1 liter of distilled water. About 8.76 grams of NaCl is added to an aliquot of 500 mls of the TRIS buffer to form 100 mM TRIS with 300 mM NaCl (TRIS Buffered Saline). Sodium azide is added to a final concentration of 0.2%.

About 0.25 grams of FFBSA are added to 50 milliliters of the TRIS Buffered Saline. The solution is stirred gently until dissolved to form TRIS Buffered Saline-BSA. Next about 0.5 grams of CHAPS are added to 25 milliliters of the TRIS Buffered Saline-BSA. The pH is adjusted to about 9.3. The final concentration is 100 mM TRIS, 300 mM NaCl, 0.5% BSA, 2% CHAPS and 0.2% Sodium Azide.

II. Preparation of Hemolysates from Blood
A. For the Ciba-Corning ACS™ folate assay an aqueous solution of 0.4% Ascorbic Acid (Aldrich) is prepared. One hundred microliters of blood from each sample is combined with 1 milliliter of the 0.4% ascorbic acid solution. The samples are stored frozen at −20 C. until the assay is performed.

III. Preparation of Samples for Assay from Hemolysates
A. For the ACS assay, the samples are thawed and 100 microliters of the hemolysates are diluted with one hundred microliters of the Hemolysate Diluent, prepared as described in Example 3 Section I.

IV. Assay of the Samples
A. The samples as prepared in Example 3 Section IIIA, are assayed according to the package insert for the ACS assay. Appropriate controls are analyzed for the assay.

EXAMPLE 4

The effects of adding protein to the diluent were investigated.
I. Preparation of Hemolysate Diluent
A. Materials:
  TRIS: molecular weight 121.1
  NaCl: molecular weight 58.44
  CHAPS: Sigma Chemical Co.
  Folate-free BSA: Intergen Inc.
B. Preparation of Diluent.
  Control diluent was prepared as described in Example 2 I B.

Protein free diluent was prepared as follows: About 0.30275 grams of TRIS and 0.4383 grams of NaCl was added to about 20 milliliters of distilled water. The pH was adjusted to 9.3. About 1 gram of CHAPS was added and the total volume was adjusted to about 40 milliliters. The pH was rechecked. No adjustment was needed. The total volume was adjusted to 50 mls.

II. Preparation of Hemolysates from Blood
A. An aqueous solution of 0.4% Ascorbic Acid (Aldrich) was prepared. One hundred microliters of blood from each sample was combined with 1 milliliter of the 0.4% ascorbic acid solution. The samples were stored frozen at −20 C. until the assay was performed.

III. Preparation of Samples for Assay from Hemolysates
A. The samples were thawed and 100 microliters of the hemolysates were diluted with one hundred microliters of the Hemolysate Diluents—one with protein and one without protein, prepared as described in Example 4 Section I.

IV. Assay of the Samples
A. The samples as prepared in Example 4 Section IIIA, were assayed according to the package insert for the Stratus assay. Appropriate controls were analyzed for the assay.

V. Results

TABLE 2

| Sample | Control Diluent | Protein-Free Diluent | Observed/ Expected |
|---|---|---|---|
| 1 | 200 | 220 | 110% |
| 2 | 220 | 250 | 114% |
| 3 | 187 | 201 | 107% |
| 4 | 429 | 419 | 96% |

Protein is not critical for the diluent.

EXAMPLE 5

Effect of Different Detergents on the Diluent
I. Preparation of Hemolysates
  Hemolysates were prepared on two different samples as described in Example 4, II A and were incubated for 90 minutes in the dark prior to use.
II. Preparation of Diluent
  Different detergents were added at a final concentration of 1% to a Stratus Neutralizing Reagent-a solution of sodium tetraborate buffer at pH 8.0 with 0.1% sodium azide.
III. Preparation of Samples from Hemolysates
  Two different samples were diluted 1:1 in a TRIS buffered saline with 5% protein based diluent containing 1% NP-40.
IV. Assay of Samples
  A Stratus Folate Assay kit was used to evaluate the samples. The neutralizing reagents prepared as described in Example 5, II were substituted for the commercial Neutralizing Reagent. The commercial Neutralizing Reagent was used as a control. In every other respect, the assay was conducted as per the manufacturer's instructions.
V. Results

TABLE 3

| Neutralizing Agent with detergent | Sample 1 | Sample 2 |
|---|---|---|
| Control (no detergent) | 7.2 | 13.0 |
| 1% Triton | 6.6 | 15.8 |

TABLE 3-continued

| Neutralizing Agent with detergent | Sample 1 | Sample 2 |
|---|---|---|
| 1% NP-40 | 8.9 | 15.3 |
| 1% Tween-20 | 6.9 | 14.7 |
| 1% CHAPSO | 5.0 | 6.7 |
| 1% BRIJ-35 | 7.0 | 14.4 |

Only CHAPSO was able to reduce the folate levels to expected results.

EXAMPLE 6

Comparison of CHAPS and CHAPSO Detergents

I. Preparation of Hemolysate Diluents

A. Materials:
   TRIS: molecular weight 121.1
   NaCl: molecular weight 58.44
   CHAPS: Sigma Chemical Co.
   Folate-free BSA: Intergen Inc.
   CHAPSO B. Preparation of Diluent.

Ten diluents were prepared as described in Example 2 I B. The differences between the diluents were as follows: One diluent contained 1% CHAPSO and 0.5% BSA, the second diluent contained 1% CHAPS and 0.5% BSA, the third diluent contained 2% CHAPSO and 0.5% BSA, the fourth diluent contained 2% CHAPS and 0.5% BSA, the fifth diluent contained 1% CHAPSO and 5% BSA, the sixth diluent contained 1% CHAPS and 5% BSA, the seventh diluent contained 2% CHAPSO and 5% BSA, the eighth diluent contained 2% CHAPS and 5% BSA, the ninth diluent contained 1% CHAPSO and 1% CHAPS and 0.5% BSA and the tenth contained 1% CHAPSO and 1% CHAPS and 5% BSA. The control contained 1% NP-40 and 5% BSA.

II. Preparation of Hemolysates

Hemolysates were prepared on two different samples, which were particularly problematic, as described in Example 4, II A and were incubated for 90 minutes in the dark prior to use.

III. Preparation of Samples

Two samples were combined 1:1 with each of the different diluents.

IV. The samples were assayed in a Stratus Assay for Folate following the manufacturer's directions.

V. Results

| Diluent | Sample 1 | Sample 1/ Bio-rad | Sample 2 | Sample 2/ Bio-rad |
|---|---|---|---|---|
| Control | 578 | 1.49 | 810 | 2.31 |
| Control | 542 | 1.40 | 835 | 2.39 |
| 1% CHAPSO 0.5% BSA | 422 | 1.09 | 575 | 1.64 |
| 2% CHAPSO 0.5% BSA | 335 | 0.87 | 406 | 1.16 |
| 1% CHAPSO 5% BSA | 388 | 1.00 | 523 | 1.49 |
| 2% CHAPSO 0.5% BSA | 338 | 0.87 | 440 | 1.26 |
| 1% CHAPSO 1% CHAPS 0.5% BSA | 330 | 0.85 | 415 | 1.19 |
| CONTROL | 423 | 1.09 | 777 | 2.22 |
| CONTROL | 537 | 1.39 | 801 | 2.29 |
| 1% CHAPS | 388 | 1.00 | 608 | 1.74 |
| 0.5% BSA 2% CHAPS | 314 | 0.81 | 413 | 1.18 |
| 0.5% BSA 1% CHAPS 5% BSA | 301 | 0.78 | 590 | 1.69 |
| 2% CHAPS 5% BSA | 296 | 0.76 | 462 | 1.32 |
| 1% CHAPS 1% CHAPSO 5% BSA | 272 | 0.70 | 414 | 1.18 |

CHAPS and/or CHAPSO at 2% is best for the samples.

EXAMPLE 7

The effects of buffer concentration and salt concentrations were determined.

I. Preparation of Hemolysate Diluents

The stock solutions described in Example 1 were used to prepare a variety of diluents. The concentrations of each reagent are as follows:

| Diluent # | [TRIS] mM | [NaCl] mM | BSA % | CHAPS % |
|---|---|---|---|---|
| 1 | 1000 | 500 | 5 | 2 |
| 2 | 505 | 500 | 5 | 2 |
| 3 | 10 | 500 | 5 | 2 |
| 4 | 1000 | 0 | 5 | 2 |
| 5 | 505 | 0 | 5 | 2 |
| 6 | 505 | 1000 | 5 | 2 |
| 7 | 1000 | 1000 | 5 | 2 |
| 8 | 10 | 1000 | 5 | 2 |
| 9 | 10 | 0 | 5 | 2 |
| 10 (CNTRL) | 50 | 150 | 5 | 2 |

II. Preparation of Hemolysates

Hemolysates were prepared on a single sample, as described in Example 4, II A and were incubated for 90 minutes in the dark prior to use.

III. Preparation of Samples

Two samples were combined 1:1 with each of the ten different diluents.

IV. The samples were assayed in a Stratus Assay for Folate following the manufacturer's directions.

V. Results

| Diluent # | Result | ratio of experimental/ control |
|---|---|---|
| 1 | 220 | 0.92 |
| 2 | 199 | 1.02 |
| 3 | 195 | 1.04 |
| 4 | 239 | 0.85 |
| 5 | 228 | 0.89 |
| 6 | 152 | 1.34 |
| 7 | 170 | 1.19 |
| 8 | 175 | 1.16 |
| 9 | 212 | 1.04 |
| 10 | 203 | 1 |

The amount of salt and TRIS does not have an effect on the diluent. TRIS may be used at a range from 0.01M to 1M and NaCl may be used at a range from 0 to at least about 0.5M.

We claim:

1. A composition useful for the determination of folate from a hemolysate of red blood cells in a non-radiolabeled assay comprising:

a) a detergent; and b) a buffer;

wherein the composition solubilizes membranes of red blood cells in the hemolysate and allows for the determination of folate in said non-radiolabeled assay.

2. The composition of claim 1 further comprising a salt.

3. The composition of claim 1 further comprising an inert protein.

4. The composition of claim 1 wherein the label of the non-radiolabeled assay is selected from the group consisting of enzymes, colorimetric molecules, fluorometric molecules and chemiluminescent molecules.

5. The composition of claim 1 wherein the detergent is selected from the group consisting of (3-{3-cholamidopropyl)dimethyl-ammonio}-1-propanesulfonate), (3-[3-cholamidopropyl)-dimethylammonio-2-hydroxy-1-propanesulfonate), and N-dodecyl-N,N-dimethyl-3-ammonio-1-propanesulfonate.

6. The composition of claim 1 wherein the buffer has a buffering capacity from pH 8 to pH 10.

7. The composition of claim 1 wherein the buffer is selected from the group consisting of TRIS, borate buffers, sodium or potassium phosphate buffers, 3-[N,N-bis(2-Hydroxyethyl)amino]-2-hydroxy-propanesulfonic acid (DIPSO), 3-[N-tris(hydroxymethyl)methylamino]-2-hydroxypropanesulfonic acid] (TAPSO), N-[2-hydroxyethyl}piperazine-N'-[2-hydroxy-propanesulfonic acid] (HEPPSO), Piperazine-N,N'-bis[2-hydroxypropanesulfonic acid] (POPSO, N-[2-hydroxyrthyl][piperazine-N'-[3-propanesulfonic acid} (EPPS), Triethanolamine (TEA), Tricine, Bicine, and N-tris[hydroxymethyl]methyl-3-aminopropanesulfonlc acid; ([2-hydroxy-1,1-bis(hydroxymethyl)-ethyl]amino)-1-propanesulfonic acid) (TAPS).

8. The composition of claim 2 wherein the salt is selected from the group consisting of sodium chloride, potassium chloride, sodium sulfate, sodium bromide, potassium bromide, calcium chloride, barium sulfate, barium chloride, and lithium chloride.

9. The composition of claim 3 wherein the inert protein is selected from the group consisting of albumin, ovalbumin and gelatin.

10. A composition useful for the determination of folate from a hemolysate of red blood cells in a non-radiolabeled assay comprising an aqueous solution of:

a) a zwitterionic detergent that solubilizes red cell membranes;

b) a buffer wherein the buffer has a buffering capacity from pH 8 to 10;

c) a salt; and d) an inert protein selected from the group consisting of albumin, ovalbumin, and gelatin.

11. The composition of claim 10 wherein the buffer is TRIS, the salt is sodium chloride, and the protein is bovine serum albumin.

12. A composition useful for the determination of folate from a hemolysate of red blood cells in a non-radiolabeled assay comprising:

a) a detergent selected from the group consisting of (3-{3-cholamidopropyl)dimethyl-ammonio}-1-propanesulfonate), (3-[3-cholamidopropyl)-dimethylammonio-2-hydroxy-1-propanesulfonate), and N-dodecyl-N,N-dimethyl-3-ammonio-1-propanesulfonate;

b) a buffer wherein the buffer has a buffering capacity from pH 8 to 10;

c) a salt; and d) an inert protein selected from the group consisting of albumin, ovalbumin, and gelatin.

13. The composition of claim 12 wherein the buffer is TRIS, the salt is sodium chloride, and the protein is bovine serum albumin.

14. A method to prepare a hemolysate for the determination of folate in red cells comprising:

a. combining an effective amount of the composition of claim 1 and the hemolysate to form a mixture; and b. assaying an aliquot of the mixture in a non-radiolabeled assay.

15. The method of claim 14 wherein the label of the non-radiolabeled assay is selected from the group consisting of colorimetric molecules, fluorometric molecules, enzymes and chemiluminescent molecules.

16. The method of claim 15 wherein the non-radiolabeled assay utilizes a solid phase and said solid phase is a porous matrix wherein the material of the porous matrix is selected from the group consisting of cellulose, paper, and glass fiber.

17. A method to prepare a hemolysate for the determination of folate in red cells comprising:

a. combining an effective amount of the composition of claim 10 and the hemolysate to form a mixture; and b. assaying an aliquot of the mixture in a non-radiolabeled assay.

18. The method of claim 17 wherein the label of the non-radiolabeled assay is selected from the group consisting of colorimetric molecules, fluorometric molecules, enzymes and chemiluminescent molecules.

19. The method of claim 18 wherein the non-radiolabeled assay utilizes a solid phase and the solid phase is a porous matrix wherein the material of the porous matrix is selected from the group consisting of cellulose, paper, and glass fiber.

20. A method to prepare a hemolysate for the determination of folate in red cells comprising:

a. combining an effective amount of the composition of claim 12 and the hemolysate to form a mixture; and b. assaying an aliquot of the mixture in a non-radiolabeled assay.

21. The method of claim 20 wherein the label of the non-radiolabeled assay is selected from the group consisting of colorimetric molecules, fluorometric molecules, enzymes and chemiluminescent molecules.

22. The method of claim 21 wherein the non-radiolabeled assay utilizes a solid phase and the solid phase is a porous matrix wherein the material of the porous matrix is selected from the group consisting of cellulose, paper, and glass fiber.

* * * * *